(12) United States Patent  
Schwarzbich

(10) Patent No.: US 7,637,888 B2
(45) Date of Patent: Dec. 29, 2009

(54) SYRINGE

(76) Inventor: Jörg Schwarzbich, Wertherstrasse 15, Bielefeld (DE) 33615

( * ) Notice: Subject to any disclaimer, the term of this patent is extended or adjusted under 35 U.S.C. 154(b) by 282 days.

(21) Appl. No.: 11/572,225

(22) PCT Filed: May 14, 2005

(86) PCT No.: PCT/EP2005/005303

§ 371 (c)(1),
(2), (4) Date: Jan. 17, 2007

(87) PCT Pub. No.: WO2006/010393

PCT Pub. Date: Feb. 2, 2006

(65) Prior Publication Data

US 2008/0021388 A1 Jan. 24, 2008

(30) Foreign Application Priority Data

Jul. 22, 2004 (DE) .................. 20 2004 011 516 U

(51) Int. Cl.
*A61M 5/00* (2006.01)
*A61M 5/32* (2006.01)
*A61M 5/315* (2006.01)
(52) U.S. Cl. .................. 604/110; 604/195; 604/240
(58) Field of Classification Search ............... 604/187, 604/110, 192–198, 220, 218, 240, 243
See application file for complete search history.

(56) References Cited

U.S. PATENT DOCUMENTS

| 4,507,117 | A |   | 3/1985  | Vining et al. |
| 5,205,824 | A | * | 4/1993  | Mazur ................... 604/110 |
| 5,378,240 | A |   | 1/1995  | Curie et al. |
| 5,997,511 | A | * | 12/1999 | Curie et al. .............. 604/195 |
| 7,530,966 | B2 | * | 5/2009 | Woehr et al. ............. 604/110 |

FOREIGN PATENT DOCUMENTS

| WO |    9744076 A |    | 11/1997 |
| WO | WO 9744076   | *  | 11/1997 |

* cited by examiner

*Primary Examiner*—Matthew F Desanto
(74) *Attorney, Agent, or Firm*—Richard M. Goldberg

(57) ABSTRACT

A syringe includes a piston (16) that is slidably guided in a casing (10), and a needle (20) adapted to be withdrawn into the casing. The piston (16) and the needle (20) are connected by a coupling (22; 22') which is adapted to assume three states: a releasable coupling state in which the needle (20) can be moved towards the front end of the casing (10) together with the piston (16), an uncoupled state in which the piston (16) can be moved back in the casing (20) separately from the needle (20), and a permanent coupling state in which the needle (20) can be withdrawn into the casing (10) by the piston (16).

12 Claims, 3 Drawing Sheets

SYRINGE

BACKGROUND OF THE INVENTION

The invention relates to a syringe comprising a piston that is slidably guided in a casing, and a needle adapted to be withdrawn into the casing.

Injection syringes for the administration of medicine or vaccine are preferably configured as one-way syringes that are to be disposed after they have been used once, and wherein a mechanism assures that they are non-usable after the first use, so as to avoid infections caused by a repeated use of the syringe. However, there is a risk that the unprotected needle of the syringe causes injuries and hence infections during or after the disposal of the syringe. In order to reduce the risk of injury, it has been common practice to mount a protective cap on the needle after the syringe has been used, so that the needle is protected in the condition in which the syringe is disposed of. Frequently, however, it is just the process of mounting the protective cap that leads to injuries.

In practice, injection syringes have become known, wherein the needle is elastically biased, so that it automatically retreats into the casing after the syringe has been used. This, however, requires a relatively complex triggering mechanism which increases the production costs of the syringes. However, disposable syringes for mass vaccinations or for the combat of endemic diseases, in particular in the third world, should be producible at low costs.

SUMMARY OF THE INVENTION

It is therefore an object of the invention to provide a disposable syringe that can be produced at low costs and offers an improved safety.

According to the invention, this object is achieved by the feature that the piston and the needle are connected by a coupling which assumes three states: a releasable coupling state in which the needle can be moved together with the piston towards the front end of the casing, an uncoupled state, in which the piston is separated from the needle and can be withdrawn into the casing, and a permanent coupling state, in which the needle can be withdrawn into the casing by means of the piston.

In a delivery state of the syringe, the coupling is in the releasable coupling state, and the piston is withdrawn, so that the needle is protected in the interior of the casing. Thus, the risk of injuries is reduced even in the state prior to the use of the syringe.

When the syringe is to be used, the user pushes the piston towards the front end, so that the needle is projected out of the casing. Then, the tip of the needle can be immersed into the vaccine or medicine, as usual, and the liquid can be sucked into the casing of the syringe by withdrawing the piston. During the withdrawal movement of the piston, the coupling transits into the uncoupled state, so that the needle remains in its projected position relative to the casing, and the piston alone is moved rearwards. Then, during the proper injection process, the piston is again moved forward, until the coupling parts of the piston and the needle are finally re-engaged with one another. During this process, the coupling assumes the permanent coupling state in which the needle and the piston are persistently connected to one another. When, now, the user or an unauthorized third person attempts to suck-in liquid once again, the needle moves rearward into the casing together with the piston, so that no subatmospheric pressure can be built up in the casing and, consequently, no liquid can be sucked-in. In this way, the syringe is protected against re-use. At the same time, the permanent coupling state has the advantage that the needle can be withdrawn again into the casing by means of the piston, without any risk that the user is injured by the tip of the needle. Then, in the disposal condition, the needle is again protected in the interior of the casing, so that other persons can no longer be injured or infected by the needle, neither.

Useful embodiments and further developments of the invention are indicated in the dependent claims.

For the coupling that goes sequentially through the three states described above, several embodiments are conceivable which can easily be implemented by injection molding techniques. Preferably, the permanent coupling state is established by a snap connection with tensile strength between the needle and the piston. In contrast, in the releasable coupling state, an elastically biased element establishes a thrust-resistant connection between the piston and the needle, so that the needle will be pushed forward by the piston without establishing the snap connection that defines the permanent coupling state. When the piston is withdrawn, the elastically biased element is relaxed, so that, now, the snap connection for the permanent coupling state can be established as soon as the coupling members of the needle and the piston are again brought into engagement with one another.

Preferably, a coupling member, that is formed at the rear end of the needle, and the casing of the syringe have such a configuration that they can be snap-fastened to one another in a fluid-tight manner when the needle is in its front terminal position. In this way, the needle can be fixed in the casing in the foremost position, and it is assured that the coupling makes a transition from the releasable coupling state into the uncoupled state when the piston is withdrawn in the process of loading the syringe, i.e. when the liquid is sucked-in. At the same time, the fluid-tight connection makes it possible to build up a subatmospheric pressure in the casing and, accordingly, to suck-in the liquid. The snap connection between the needle and the casing is dimensioned such, that the resistance that is experienced when the needle penetrates into the body of the patient is not sufficient for releasing the snap connection, whereas, in the permanent coupling state, the snap connection between the needle and the piston is so strong that the needle can again be freed of its snap connection with the casing.

The elastically biased element is preferably formed by at least one elastic tongue that, when in the biased state, acts as a spacer between the coupling member of the needle and the coupling member of the piston. When the elastic tongue is relaxed while the piston is withdrawn, it assumes a position in which it can plunge into a recess of the respective other coupling member, so that it does no longer act as a spacer and permits to establish the snap connection for the permanent coupling state.

In a preferred embodiment, the casing is internally formed with a lock which, in a manner known per-se, forms a stop or detent when the piston is withdrawn in the process of loading the syringe, in order to prevent the piston from being drawn back too far. When, after the injection, the syringe is transformed into the disposal state, this detent can however be overcome by applying a certain force, and then the lock prevents the needle from being moved forward again. Thus, it is assured that the needle is permanently accommodated and protected inside of the casing in the disposal state.

In a modified embodiment, the coupling has such a configuration that it provokes a slightly inclined position of the needle in the permanent coupling state, so that the tip of the needle will abut a shoulder at the front end of the casing and can no longer be projected out of the casing once it has been withdrawn after the injection process.

BRIEF DESCRIPTION OF THE DRAWINGS

Embodiment examples of the invention will now be described in detail in conjunction with the drawings, wherein.

DETAILED DESCRIPTION

Figure 1:
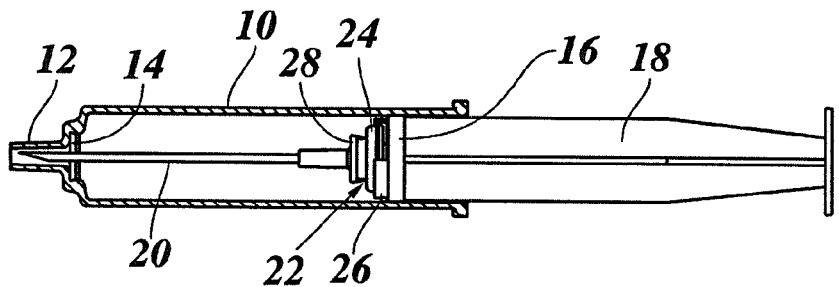
FIGS. 1 to 5 are axial sectional views of a syringe in different stages prior to, during, and after an injection process.

The syringe shown in FIG. 1 comprises a cylindrical casing 10 of plastics that is constricted at its front end to form a spout 12. A lock in the form of a peripheral annular groove 14 is formed in the internal wall of the casing in the transition zone between the spout 12 and the main body of the casing 10.

A disk-shaped piston 16 is formed at the front end of a piston rod 18 and is guided to be slidable in the cylindrical part of the casing 10.

In the condition shown in FIG. 1, a needle 20 is accommodated in the interior of the casing 10 in such a manner that the tip thereof is accommodated and protected in the spout 12. The rear end of the needle 20 is connected to the piston 10 by a coupling 22. The coupling 22 comprises a needle-side coupling member 24 and a piston-side coupling member 26. In FIG. 1, these coupling members are in a releasable coupling state in which a thrust-resistant connection between the piston and the needle is formed, which connection, however, is releasable when the piston 16 is withdrawn. The needle-side coupling member 24 has an annular boss 28 forming the complement of the annular groove 14 of the casing 10.

Figure 2:
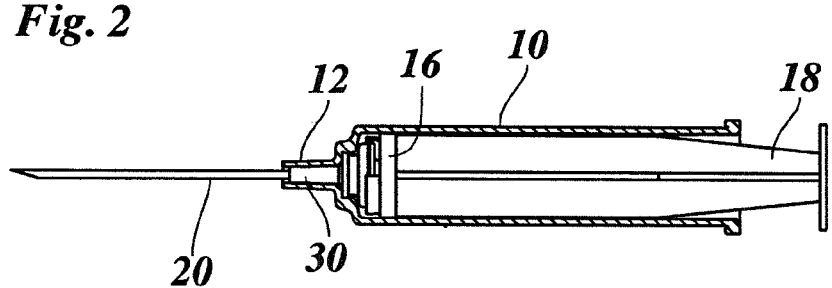

The condition of the syringe shown in FIG. 1 corresponds to the delivery state. When the syringe is to be transformed into a condition ready for use, which is shown in FIG. 2, the user pushes the piston 16 forward by means of the piston rod 18. During this process, the needle 20 is projected out of the casing, and the boss 28 is locked in the annular grove 14, so that the needle 20 is locked in the casing with a certain retention force by means of the coupling member 24. Then, a cone 30 formed on the coupling member 24 fits in the spout 12, so that the cavity delimited by the piston 16 in the front part of the casing 10 is sealed-off at the front end, to one part by engagement of the peripheral wall of the cone 30 at the internal surface of the spout 12, and to the other part by engagement of the boss 28 in the annular grove 14. At the same time, in this way, the needle 20 is stably held in the casing 10.

Figure 3:
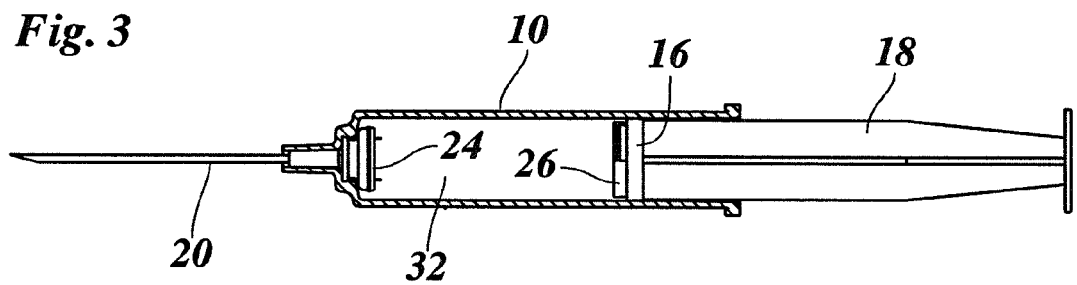

In order to load the syringe, the user withdraws the piston rod 18 into the position shown in FIG. 3. During this, the coupling members 24, 26 may be disengaged from one another, so that the piston 16 travels backward alone, whereas the needle 20 remains snap-fastened to the casing 10 by the coupling member 24. Since the cavity 32 in the interior of the casing 10 is sealed fluid-tightly, the liquid to be injected is sucked-in through the interior of the needle 20.

Then, the user pricks the tip of the needle 20 into the skin of the patient and pushes the piston rod 18 forward again in order to inject the liquid into the body of the patient. The retaining force of the lock formed by the boss 28 and annular grove 14 is so large that the needle, when penetrating into the body, will not retreat but will retain its position relative to the casing 10. During the injection process, the user may repeatedly move the piston rod 18 and the piston 16 back and forth, and this will not compromise the function of the syringe.

Figure 4:
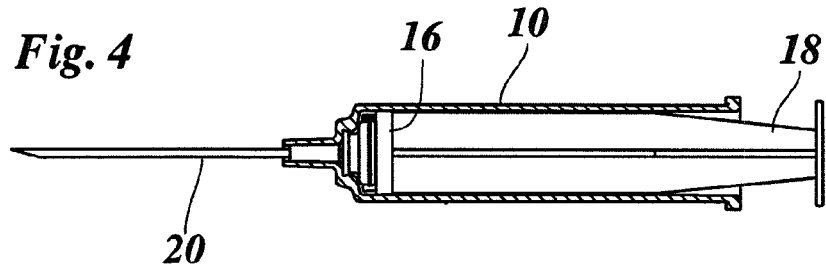

In FIG. 4, the injection process is completed, and the piston 16 has reached its front terminal position in the casing 10. The coupling members 24, 26 have again been brought into engagement with one another, but, because of a mechanism that will be described below, they now form a permanent snap connection. The strength of this snap connection is larger than the strength of the snap connection between the needle 20 and the casing 10 formed by the boss 28 and the annular grove 14.

Figure 5:
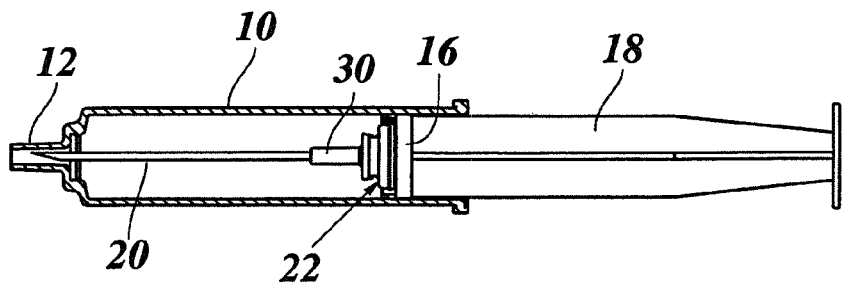

When the needle 20 has been withdrawn from the skin of the patient, and the user wants to dispose of the syringe, he withdraws the piston rod 18 into the position shown in FIG. 5. Thanks to the permanent snap connection between the coupling members 24, 26, the needle 20 is now entrained rearward, until the tip thereof is again protected in the spout 12 of the casing. This avoids the risk that anybody is injured by the tip of the needle. When a user or an unauthorized third person now moves the piston rod 18 and the piston 16 forward again and attempts to load the syringe once again, the permanent snap connection persists, and when the piston is withdrawn, the needle 20 is also moved rearward again. In this process, the cone 30 retreats from the spout 12, and air may enter into the interior of the casing 10 through an annular gap formed between the needle 20 and the internal surface of the spout 12, so that no subatmospheric pressure can be built-up in the interior of the casing and, consequently, no liquid can be sucked-in. In this way, a forbidden re-use of the syringe is prevented.

Figure 6:
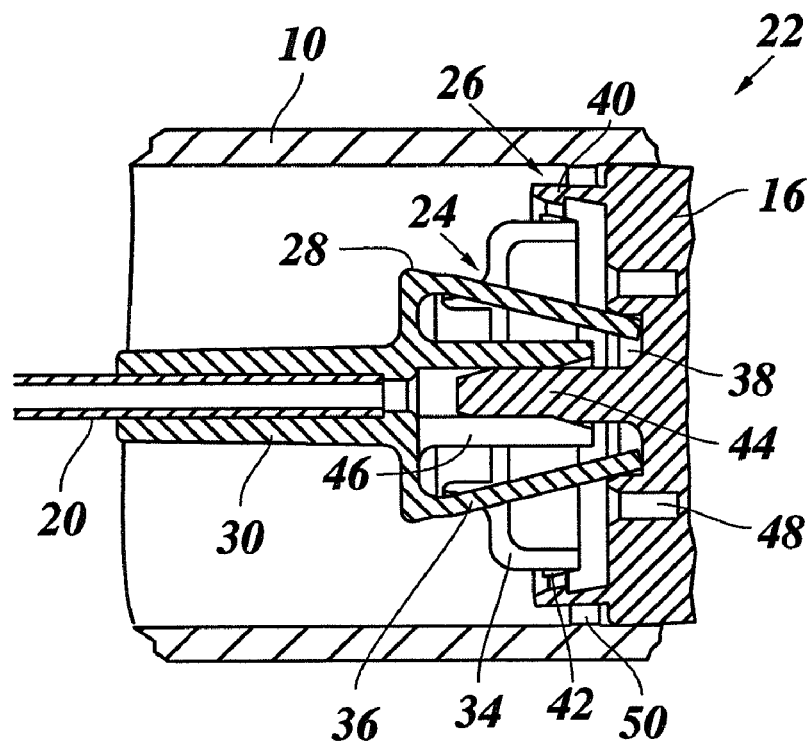
FIG. 6 is an enlarged axial section of a coupling between a needle and a piston of the syringe in a releasable coupling state.
Figure 7:
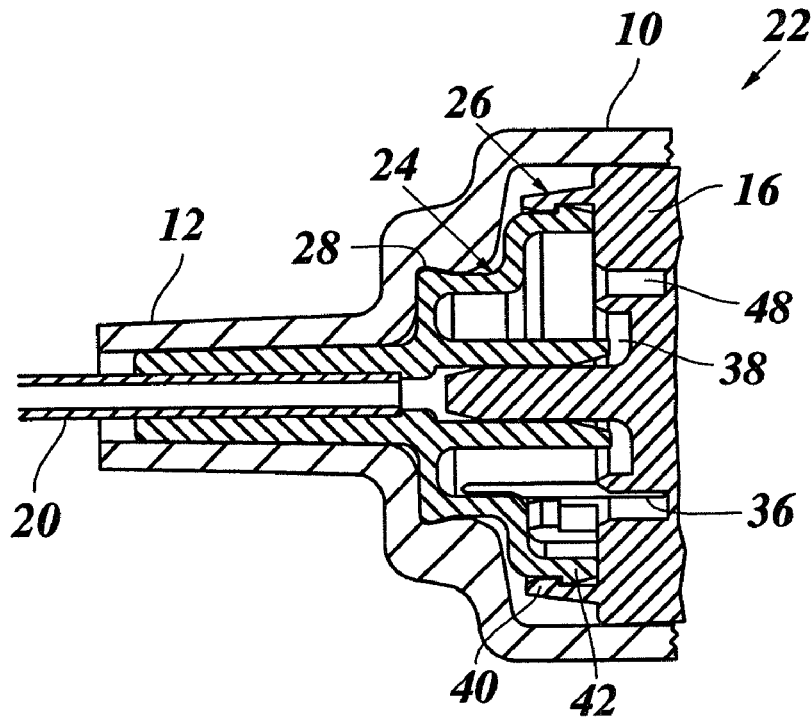
FIG. 7 is a sectional view of the coupling in a permanent coupling state, in a sectional plane that is rotated in comparison to FIG. 6.

The coupling 22 has been shown in greater detail in FIGS. 6 and 7. FIG. 6 shows the coupling in the releasable coupling state corresponding to FIG. 1. The coupling member 24, as a whole, is shaped like a bell which opens towards the piston 16 and the peripheral wall of which is penetrated in at least two positions by cut-outs 34. Each of these cut-outs 34 accommodates an elastic tongue 36 that is formed integrally with the coupling member 24 and projects freely towards the piston 16. In the condition shown in FIG. 6, the tongues 36 are slightly compressed, and they are held with elastic bias in a recess 38, e.g. an annular groove of the piston 16. In this condition, the tongues 36 act as spacers between the piston 16 and the coupling member 24. The piston-side coupling member 26 is formed directly on the front side of the piston and forms a collar that surrounds the bell-shaped needle-side coupling member 24 on a portion of the periphery thereof and has a profile shaped as an inwardly cranked locking lug 40. Corresponding counter-locks 42 are formed at the outer periphery of the bell-shaped coupling member 24. In the condition shown in FIG. 6, however, the elastic tongues 36 prevent the lugs 40 from gripping behind the counter-locks 42. The lugs 40 will only slide onto the counter-locks 42 with their ramp surfaces (this occurs in a peripheral portion that is not visible in FIG. 6), whereby the collar is slightly expanded. When the piston 16 is thrust forward (to the left in FIG. 6) by means of the piston rod 18, the thrust force is transmitted by the elastic tongues 36 onto the coupling member 24 and further onto the needle 20, so that the piston and the needle move forward together without allowing the lugs 40 to lock at the counter-locks 42. During this process, a stable guidance for the needle 20 is assured by a pin 44, which centrally projects from the piston 16, engaging into a sleeve 46 formed in the interior of the coupling member 24. At the same time, the pin 44 and the sleeve 46 provide for frictional contact by which the coupling is held in the state illustrated in FIG. 6.

When now, after the coupling member 24 has reached its foremost position and has been locked with the boss 28 in the annular grove 14 of the casing, the piston 16 is withdrawn again, the free ends of the elastic tongues 36 retreat from the recess 38, and they spring back into a relaxed position in which the extend essentially in parallel to one another. In this position, the free ends of the tongues 36 are aligned with deeper recesses 48 of the piston. When, then, the piston 16 reaches again the foremost position at the end of the injection process, the free ends of the elastic tongues 36 enter into the recesses 48, so that they do no longer act as spacers. For this reason, the distance between the coupling members 26 and 24 can be reduced to such an extent that the locking lugs 40 slide over the counter-locks 42 and lock behind the same, as has been shown for a different sectional plane in FIG. 7. The lower part of FIG. 7 also shows the edge of one of the elastic tongues 36 with its free end accommodated in the recess 48. In this condition, the lugs 40 and counter-locks 42 connect the coupling members 24, 26 in a manner to resist tensile strain, so that the piston 16 and the needle 20 are now non-releasably connected to one another. As a consequence, when the piston is withdrawn, the boss 28 of the coupling member 24 is separated from the annular grove 14 of the casing 10.

The collar-shaped coupling member 26 and the counter-locks 42 of the coupling member 24 are all formed only on a part of the periphery. When the coupling members are produced by injection molding, this permits an easy demolding of the undercuts formed by the lugs 40 and the counter logs 42. At the same time, when the coupling is mounted, there is offered the possibility to compress the elastic tongues 36 and to insert them into the annular groove or recess 38. Optionally, the lugs 40 and the counter-locks 42 can be angularly offset from one another to such an extent that they do not come into contact with one another. Subsequently, the needle-side coupling member 24 can be rotated about its longitudinal axis until the counter-locks 42 are aligned with the lugs 40. A lock which has not been shown may be used for securing the coupling members 24, 26 in this angular position, so that they may not be rotated relative to one another. Finally, the unit formed by the piston rod, the piston, the coupling and the needle, that have been pre-mounted in this way, are inserted into the casing 10 of the syringe.

As is shown in FIG. 6, the cylindrical internal wall of the casing 10 forms a flat peripheral collar 50 that serves as a stop for the piston 16. This defines the position of the piston in the delivery state as shown in FIGS. 1 and 6. When the syringe is to be used, i.e. when passing from the condition shown in FIG. 1 to the condition shown in FIG. 2, the resistance formed by the collar 50 can be overcome with a certain effort. Then, when the syringe is loaded (FIG. 3) the collar serves as a detent in the opposite direction, indicating to the user that the maximum fill volume of the syringe has been reached. The injection process can then be performed without having to overcome a detent. Then, before the syringe is disposed of, the piston 16 is again drawn back and moved beyond the collar 50, so that the piston can only be moved forward again with a certain effort. This reduces the risk that the tip of the needle projects again from the spout 12.

Figure 8:
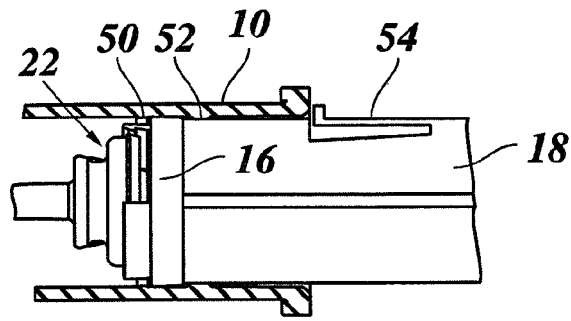
FIG. 8 is a partial sectional view of a syringe according to a modified embodiment.

FIG. 8 shows another embodiment, wherein the piston 16 is immobilized in the delivery condition (FIG. 1) between a front collar 50 and a rear collar 52. In addition, in this embodiment, the piston rod 18 forms an elastic tongue 54 which locks at the rear end of the casing 10 and must be depressed manually in order to convert the syringe from the state shown in FIG. 1 to the state shown in FIG. 2. When, after the injection, the syringe is to be converted into the disposal state (FIG. 5), the tongue 54 will again snap-in behind the end of the casing 10 and will thus prevent the needle from projecting out of the spout 12 of the casing.

Figure 9:
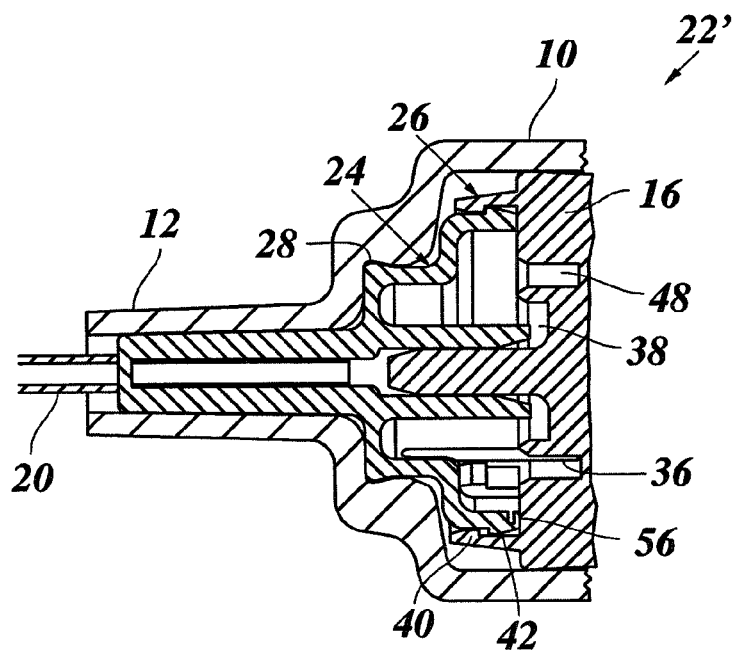
FIG. 9 is a sectional view similar to FIG. 7 for a modified embodiment of the coupling.
Figure 10:
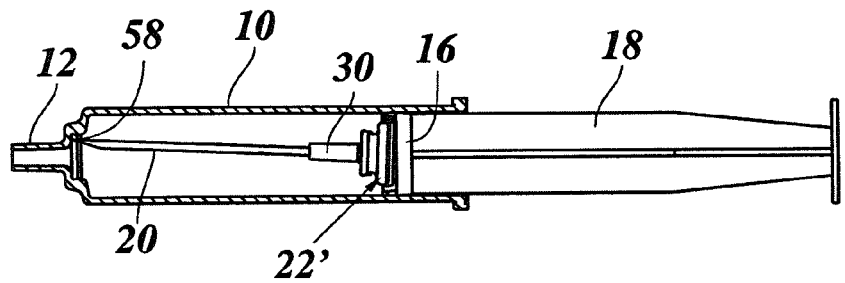
FIG. 10 is a sectional view of a syringe having the coupling shown in FIG. 9 in a disposal condition.

FIG. 9 shows a coupling 22' which differs from the coupling 22 according to FIG. 7 in that a certain play exists between the lug 40 and the counter-lock 42 on one side (bottom side in FIG. 9), and in that the lug 40 is supported at the piston 16 by an elastic tongue 56. This modification has no effect in the releasable coupling state, and the needle 20 is aligned with the spout 12, so that it may be projected out of the spout. In the condition at the end of an injection process (FIG. 4), the needle is held coaxially in the spout 12 by the cone 30, and the tongue 56 is biased elastically, as shown in FIG. 9. In this embodiment, the needle 20 is so short that it may completely be drawn out of the spout 12 when the piston rod 18 is withdrawn. Then, the elastic tongue 56 and the play of the lower lug 40 assure (in conjunction with a certain resiliency of the pin 44) that the coupling member 24 and the needle 20 assume an inclined position, as shown in FIG. 10, in which, when the piston rod is pushed forward again, the needle will no longer enter into the spout 12 but will be caught with its tip at a shoulder 58 on the front wall of the casing 10.

The invention claimed is:

1. A syringe comprising:
    a casing,
    a piston that is slidably guided in the casing, a needle adapted to be withdrawn into the casing, and
    a coupling for connecting together the piston and the needle, the coupling being adapted to assume three states in the following order:
    a releasable coupling state in which the needle is adapted to be moved towards a front end of the casing together with the piston,
    an uncoupled state in which the piston is adapted to be moved back in the casing separately from the needle, and
    a permanent coupling state in which the needle is adapted to be withdrawn into the casing by the piston
    wherein the coupling comprises:
    a locking mechanism establishing a connection with tensile strength between the piston and the needle, and
    at least one elastically biased element which, in a biased state a force is applied thereto, prevents the locking mechanism from being locked when the coupling is in the releasable coupling state, whereas, in a non-biased state, it permits an engagement of the locking mechanism when the coupling is in the permanent coupling state.

2. The syringe according to claim 1, wherein:
    the coupling comprises a needle-side coupling member and a piston-side coupling member and
    the at least one elastically biased element includes an elastic tongue which projects in an axial direction of the syringe from one said coupling member towards the other said coupling member and engages, with a free end thereof, a contour of the other said coupling member and is thereby held in a deflected, elastically biased position.

3. The syringe according to claim 2, wherein the locking mechanism is formed by inwardly cranked lugs at a collar-shaped one of said coupling members and by counter-locks on the other of said coupling members that plunges into the collar-shaped coupling member.

4. The coupling according to claim 3, wherein:
the coupling members carrying the lugs and the counter-locks are interrupted at least at one position at a periphery thereof, and
the elastic tongue is accommodated in a peripheral gap of the one said coupling member.

5. The syringe according to claim 2, wherein the elastic tongue, when in the biased state, forms a spacer between the coupling members.

6. The syringe according to claim 1, wherein the needle is adapted to be locked at the casing in a front terminal position.

7. The syringe according to claim 6, wherein:
the casing includes an internal surface with an annular groove, and
the coupling includes a coupling member for holding the needle, the coupling member including a peripheral boss adapted to be locked in the annular groove formed in the internal surface of the casing.

8. The syringe according to claim 7, wherein the casing includes a cavity which is delimited by the piston and is sealed fluid-tightly by the boss engaging in the annular groove.

9. The syringe according to claim 1, wherein:
the casing includes a spout at an end of the casing, and
the coupling includes a coupling member for holding the needle, the coupling member including a cone which is received in the spout at the end of the casing when the needle is in a front terminal position.

10. The syringe according to claim 9, wherein the casing includes a cavity which is delimited by the piston and is sealed fluid-tightly by the cone engaging in the spout.

11. The syringe according to claim 1, wherein the locking mechanism which, in the releasable coupling state and the permanent coupling state of the coupling, releasably immobilizes at least one of the piston and an associated piston rod in an axial position in which the needle is protected in an interior of the casing.

12. The syringe according to claim 1, wherein the coupling is, in the permanent coupling state, elastically biased into a position in which, when the piston is withdrawn, the needle is held in an inclined position in which a tip thereof abuts at a shoulder at a front end of the casing.

* * * * *